(12) United States Patent
Dutkiewicz

(10) Patent No.: US 6,805,126 B2
(45) Date of Patent: Oct. 19, 2004

(54) OXYGEN DELIVERY AND GAS SENSING NASAL CANNULA SYSTEM

(76) Inventor: Edward P. Dutkiewicz, 4205 Kent Dr., Largo, FL (US) 33774

( * ) Notice: Subject to any disclaimer, the term of this patent is extended or adjusted under 35 U.S.C. 154(b) by 85 days.

(21) Appl. No.: 10/096,972

(22) Filed: Mar. 14, 2002

(65) Prior Publication Data
US 2002/0112730 A1 Aug. 22, 2002

Related U.S. Application Data

(63) Continuation-in-part of application No. 09/450,695, filed on Mar. 7, 2000, now abandoned.
(60) Provisional application No. 60/110,341, filed on Dec. 1, 1998.

(51) Int. Cl.[7] ............................................. A61M 15/08
(52) U.S. Cl. .............................. 128/207.18; 128/203.22
(58) Field of Search ...................... 128/207.18, 200.26, 128/203.18, 203.22

(56) References Cited

U.S. PATENT DOCUMENTS

| | | | | |
|---|---|---|---|---|
| 2,693,800 A | * | 11/1954 | Caldwell | 128/207.18 |
| 2,931,358 A | * | 4/1960 | Sheridan | 128/207.18 |
| 3,513,844 A | * | 5/1970 | Smith | 128/207.18 |
| 4,278,082 A | * | 7/1981 | Blackmer | 128/207.18 |
| 4,422,456 A | * | 12/1983 | Tiep | 128/207.18 |
| 4,648,398 A | * | 3/1987 | Agdanowski et al. | 128/207.18 |
| 4,818,320 A | * | 4/1989 | Weichselbaum | 156/227 |
| 4,989,599 A | * | 2/1991 | Carter | 128/207.18 |
| 5,335,656 A | * | 8/1994 | Bowe et al. | 128/207.18 |
| 5,513,634 A | * | 5/1996 | Jackson | 128/207.18 |
| 5,526,806 A | * | 6/1996 | Sansoni | 128/207.18 |
| 5,682,881 A | * | 11/1997 | Winthrop et al. | 128/207.18 |
| 5,752,511 A | * | 5/1998 | Simmons et al. | 128/207.18 |

* cited by examiner

*Primary Examiner*—Henry Bennett
*Assistant Examiner*—Mital Patel

(57) ABSTRACT

An oxygen delivery and gas sensing nasal cannula system, comprising a main prong assembly and a pair of nasal prongs. There is also provided a pair of oxygen conduit tubes and a main oxygen delivery tube. There is also provided an adjustment sleeve to adjust the fit of the cannula system on a patient's head. There is also included a gas sampling, a gas sampling conduit end piece and a flared main oxygen delivery tube end piece to be receivably coupled to an oxygen supply.

2 Claims, 2 Drawing Sheets

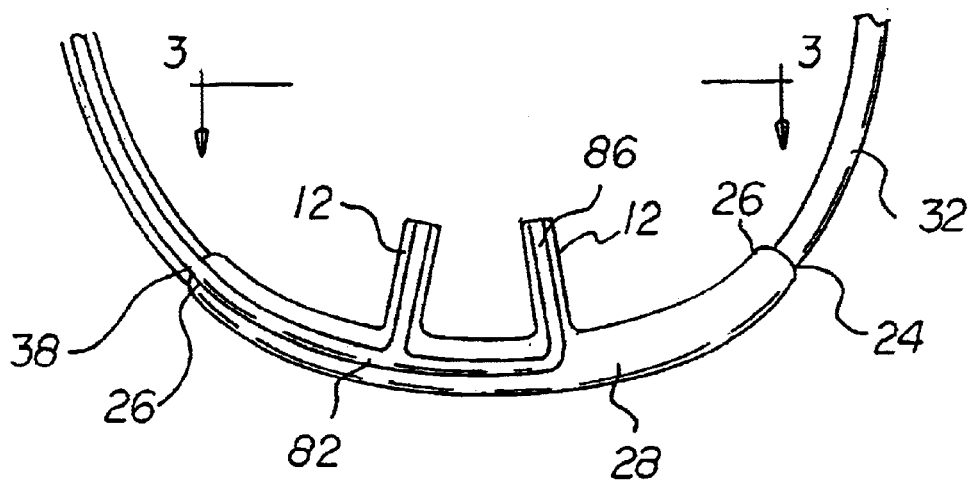
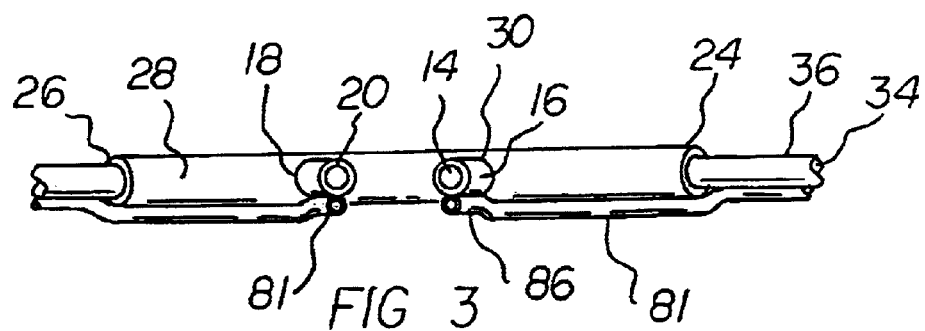
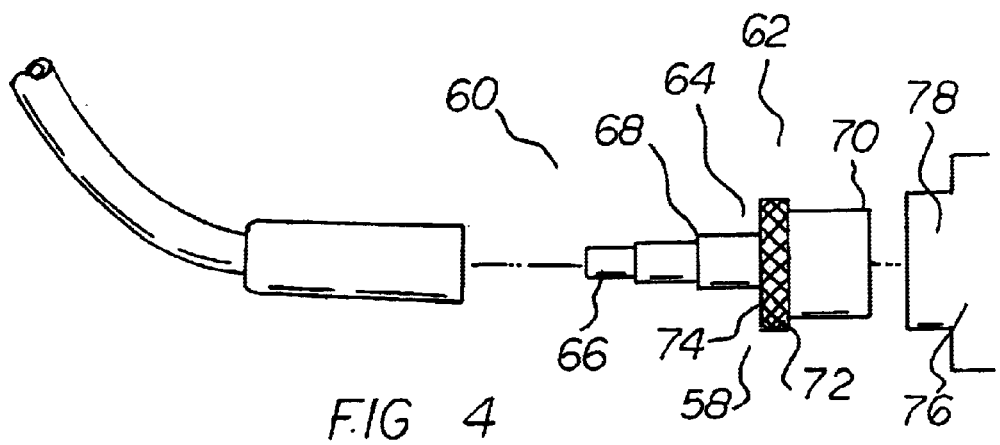

OXYGEN DELIVERY AND GAS SENSING NASAL CANNULA SYSTEM

This is a continuation in part of application Ser. No. 09/450,695 filed Mar. 7, 2000 now abandoned which claims benefit of 60/110,341 filed Dec. 1, 1998. The applicant claims the filing date of Mar. 7, 2000.

BACKGROUND OF THE INVENTION

1. Field of the Invention

The present invention relates to a an oxygen delivery and gas sensing nasal cannula system and more particularly pertains to safely and conveniently providing oxygenation and gas analysis.

2. Description of the Prior Art

The use of known methods and apparatuses is known in the prior art. More specifically, known methods and apparatuses previously devised and utilized for the purpose of providing oxygenation and analyzing gases are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,682,881 to Winthrop et al issued Nov. 4, 1997 discloses a CPAP cannula and securement apparatus. U.S. Pat. No. 5,099,836 to Rowland et al, issued Mar. 31, 1992 discloses an intermittent oxygen delivery system and cannula. U.S. Pat. No. 4,989,599 to Carter issued Feb. 5, 1991 discloses a dual lumen cannula. U.S. Pat. No. 5,335,656 to Bowe et al issued Aug. 9, 1994 discloses a providing a treating gas and sampling the exhaled gas. Lastly, U.S. Pat. No. 4,648,398 to Agdanowski et al issued Mar. 10, 1987 discloses a nasal cannula.

While these devices fulfill their respective, particular objectives and requirements, the aforementioned patents do not describe an oxygen delivery and gas sensing nasal cannula system that allows safely and conveniently providing oxygenation and gas analysis.

In this respect, the an oxygen delivery and gas sensing nasal cannula system according to the present invention substantially departs from the conventional concepts and designs of the prior art, and in doing so provides an apparatus primarily developed for the purpose of safely and conveniently providing oxygenation and gas analysis.

Therefore, it can be appreciated that there exists a continuing need for a new and improved an oxygen delivery and gas sensing nasal cannula system which can be used for safely and conveniently providing oxygenation and gas analysis. In this regard, the present invention substantially fulfills this need.

SUMMARY OF THE INVENTION

In view of the foregoing disadvantages inherent in the known types of known methods and apparatuses now present in the prior art, the present invention provides an improved an oxygen delivery and gas sensing nasal cannula system. As such, the general purpose of the present invention, which will be described subsequently in greater detail, is to provide a new and improved oxygen delivery and gas sensing nasal cannula system and method which has all the advantages of the prior art and none of the disadvantages.

To attain this, the present invention essentially comprises an oxygen delivery and gas sensing nasal cannula system for safely and conveniently providing oxygenation and gas analysis when in use. The system comprises, in combination, several components. First provided is a pair of nasal prongs. These are fabricated of a flexible elastomeric material and have a hollow round cylindrical shape. There is an internal surface and an external surface to the prongs with a wall thickness there between. Each of the nasal prongs has an inboard end and an outboard end with the outboard end being toward a user. Next provided is a main prong assembly. The assembly has a hollow round cylindrical shape with two ends. It is fabricated of a flexible elastomeric material. The assembly has an internal surface and an external surface with a wall thickness there between. The cylindrical wall of the assembly has a taper at each end, with a round body of the main prong assembly being there between. There are a pair of apertures located in the approximately midway position of the main prong assembly. The apertures are sized to firmly receive the nasal prongs. Next provided is an adhesive coupling means to secure the nasal prongs to the main prong assembly. Next provided is a pair of smaller oxygen conduit tubes. The tubes are fabricated of a flexible elastomeric material and have a round, hollow cylindrical shape. The tubes have an internal surface and an external surface with a wall thickness there between. Each of the smaller oxygen conduit tubes has an outboard end and an inboard end. The outboard end of the conduit tubes are sized to be receivably fit into, and held securely in place within, the internal diameter of the tapered end of the main prong assembly. Next provided is a main oxygen delivery tube. It is fabricated of a flexible elastomeric material and has a round, hollow cylindrical shape. The delivery tube has an internal surface and an external surface with a wall thickness there between. It also has an outboard end and an inboard end with a length there between. The main tube is sized to receive and retain the inboard ends of the pair of conduit tubes within the internal diameter of the outboard end of the main tube. Next provided is an adhesive coupling means to secure the conduit tubes within the outboard end internal diameter of the main tube. Next provided is an adjustment sleeve. The sleeve has a round hollow cylindrical configuration. It is fabricated of an elastomeric material and has an internal surface and an external surface with a wall thickness there between. The sleeve has an internal diameter sufficient to allow the adjustment sleeve to be slid with a minimal resistance along the external diameter of the main oxygen tube on to the pair of conduit tubes. The sleeve functions to tighten the cannula in place on the patient, when in use. Next provided is a flared end piece. The end piece is fabricated of an elastomeric material. It has a tapered, hollow cylindrical shape. It has an internal surface and an external surface with a wall thickness there between. The flared end piece also has an inboard end and an outboard end. The outboard end has an internal diameter sized to securely receive the external diameter of the inboard end of the main oxygen delivery tube. The inboard end is sized to have an internal diameter of between about 5 and 7 millimeters. Next provided is a gas machine adapter. The adapter is fabricated of a rigid material. It has an oxygen line portion and a gas machine portion. The oxygen line portion has a generally tapered hollow round cylindrical configuration. It has an inboard end and an outboard end. The taper of the oxygen line portion of the gas machine adapter decreases from inboard to outboard. The adapter has an internal surface and an external surface and a wall thickness there between. The internal surface is smooth and the external surface of the oxygen line portion has a series of concentric steps along the axis of the taper of the oxygen line portion. The inboard end of the oxygen line portion joins, and is coupled to, the gas machine portion. The gas machine portion of the gas machine adapter has a generally round, hollow, cylindrical shape. It has an external surface and an internal surface with a wall thickness there between. The gas machine portion has an inboard end and an outboard end. The internal diameter of the inboard gas machine portion of the adapter is between about 7 and 12 millimeters. The gas machine portion of the adapter has a knurled surface on the outboard end of the gas machine portion. The knurled surface acts to facilitate the gripping of the gas machine portion. Next provided is a gas machine with a gas machine outlet having a round hollow cylindrical configuration. The outlet has an internal surface and an external surface. The outlet has an internal diameter of between about 10 and 20 millimeters. Next provided is a gas sampling conduit. The conduit is fabricated of a flexible elastomeric material and has a generally round, hollow, cylindrical configuration. The conduit has an outside diameter of between about 1 and 4 millimeters. The conduit has an internal surface and an external surface and a wall thickness of between. The thickness of the wall is between about 1 and 3 millimeters. The conduit has an inboard end and an outboard end. The gas sampling conduit has an overall length of between about 4 and 6 feet. The outboard end has a pair of conduit nasal prongs. These prongs are oriented perpendicular to the long axis of the cylindrical hollow gas sampling conduit. Next provided is an adherent means by which the gas sampling prongs are aligned with, and adherent to, the nasal prongs. The adherent means couples the gas sampling conduit in alignment with the oxygen conduit tube. The gas sampling conduit runs with, and is adherent to, the oxygen conduit tube to the point of juncture with the main oxygen delivery tube. The gas sampling conduit passes through, and is contained within, the adjustment sleeve. The gas sampling conduit then runs with, and is adherent to, the main oxygen tube to a point between about 10 and 15 inches from the inboard end. The adherent means keeps the gas sampling conduit coupled to the external surface of the nasal oxygen prongs, oxygen conduit and main oxygen tube. Next provided is a gas sampling conduit end piece. The end piece has a generally hollow, round cylindrical configuration. It has an internal surface and an external surface and a wall thickness there between. The end piece has an inboard end and an outboard end. The outboard end has an internal diameter sized to receive and securely hold the inboard end of the gas sampling conduit. The inboard end of the end piece has a female thread on the internal surface and is configured to receive a luer locking connector. Lastly, there is provided a capnograph. The capnograph has a male luer lock connector to receive, and mate with, the female luer locking connector of the conduit end piece.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved an oxygen delivery and gas sensing nasal cannula system which has all of the advantages of the prior art known methods and apparatuses and none of the disadvantages.

It is another object of the present invention to provide a new and improved oxygen delivery and gas sensing nasal cannula system which may be easily and efficiently manufactured and marketed.

It is further object of the present invention to provide a new and improved oxygen delivery and gas sensing nasal cannula system which is of durable and reliable constructions.

An even further object of the present invention is to provide a new and improved oxygen delivery and gas sensing nasal cannula system which is susceptible of a low cost of manufacture with regard to both materials and labor, and which accordingly is then susceptible of low prices of sale to the consuming public, thereby making such an oxygen delivery and gas sensing nasal cannula system economically available to the buying public.

Even still another object of the present invention is to provide an oxygen delivery and gas sensing nasal cannula system for safely and conveniently providing oxygenation and gas analysis.

Lastly, it is an object of the present invention to provide a new and improved oxygen delivery and gas sensing nasal cannula system, comprising several components. First provided is a pair of nasal prongs. Next provided is a main prong assembly having a hollow round cylindrical shape with a taper at each end and a pair of apertures. Next provided is an adhesive means to couple the nasal prongs and the main prong assembly. Next provided is a pair of smaller oxygen conduit tubes. Next provided is a main oxygen delivery tube. Next provided is an adhesive coupling means to secure the smaller conduit tubes within the main tube. Next provided is an adjustment sleeve. Next provided is a gas sampling conduit. Next provided is a gas sampling conduit end piece. Next provided is an adherent means to couple the gas conduit and main tube. Lastly provided is a flared main oxygen delivery tube end piece.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 shows a planar view of the cannula and gas machine outlet adapter, gas machine outlet and capnograph.

FIG. 3 shows the elevation taken along line 3—3 of FIG. 2.

FIG. 4 is a side elevation of the association of the main oxygen line, the adapter and the gas machine outlet.

The same reference numerals refer to the same parts throughout the various Figures.

DESCRIPTION OF THE PREFERRED EMBODIMENT

Figure 1:
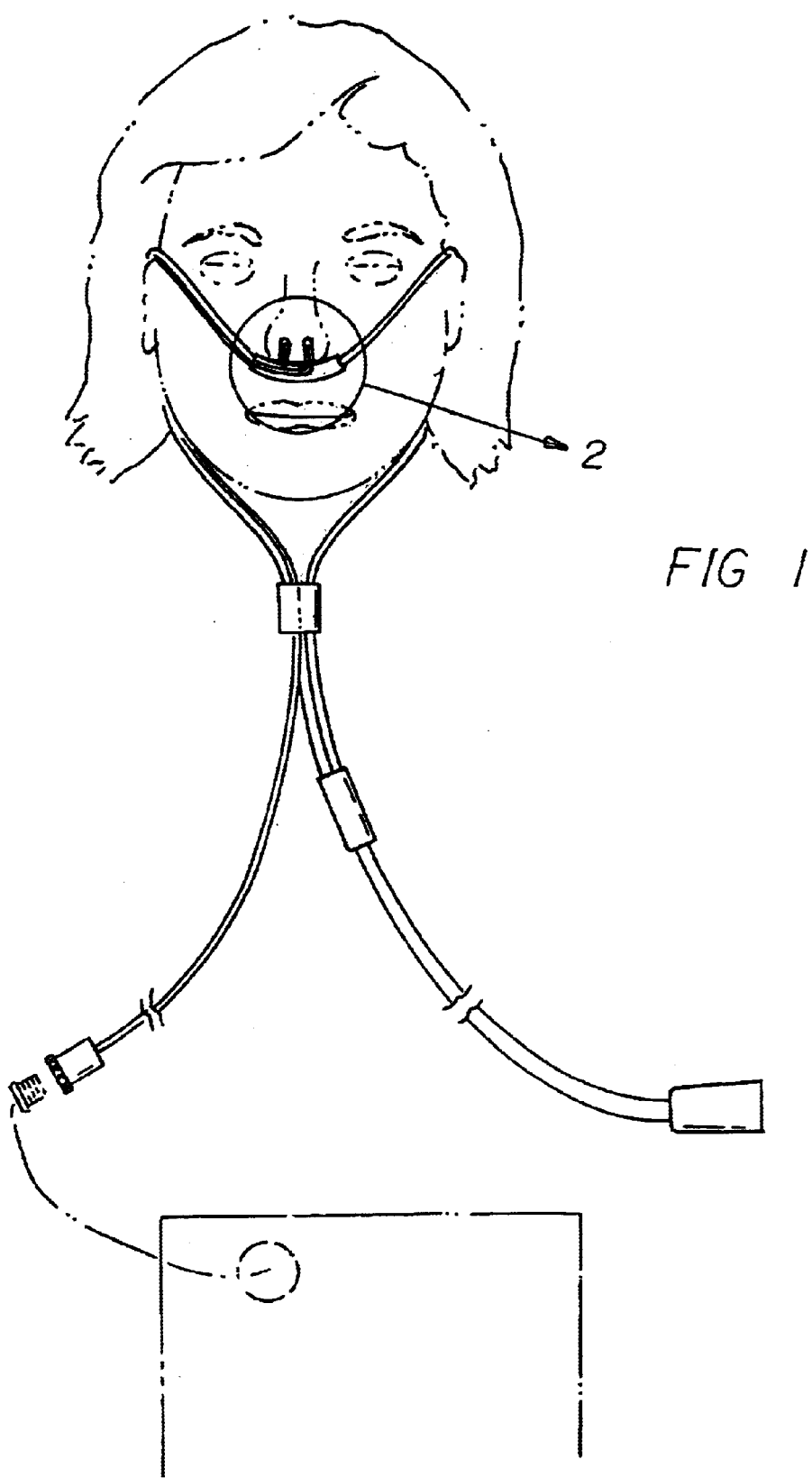
FIG. 1 is shows the oxygen delivery and gas sensing cannula in place, as utilized by a patient.

With reference now to the drawings, and in particular to FIG. 1 thereof, the preferred embodiment of the new and improved an oxygen delivery and gas sensing nasal cannula system embodying the principles and concepts of the present invention and generally designated by the reference numeral 10 will be described.

The present invention, the an oxygen delivery and gas sensing nasal cannula system 10 is comprised of a plurality of components. Such components in their broadest context include a gas machine, a capnograph, a oxygen delivery system and a gas sensing conduit. Such components are individually configured and correlated with respect to each other so as to attain the desired objective.

An oxygen delivery and gas sensing nasal cannula system 10 for safely and conveniently providing oxygenation and gas analysis when in use. The system comprises, in combination, several components.

First provided is a pair of nasal prongs 12. These are fabricated of a flexible elastomeric material and have a hollow round cylindrical shape. There is an internal surface 14 and an external surface 16 to the prongs with a wall thickness there between. Each of the nasal prongs has an inboard end 18 and an outboard end 20 with the outboard end being toward a user.

Next provided is a main prong assembly 22. The assembly has a hollow round cylindrical shape with two ends 24. It is fabricated of a flexible elastomeric material. The assembly has an internal surface and an external surface with a wall thickness there between. The cylindrical wall of the assembly has a taper 26 at each end, with a round body of the main prong assembly 28 being there between.

There are a pair of apertures 30 located in the approximately midway position of the main prong assembly. The apertures are sized to firmly receive the nasal prongs.

Next provided is an adhesive coupling means to secure the nasal prongs to the main prong assembly.

Next provided is a pair of smaller oxygen conduit tubes 32. The tubes are fabricated of a flexible elastomeric material and have a round, hollow cylindrical shape. The tubes have an internal surface 34 and an external surface 36 with a wall thickness there between. Each of the oxygen conduit tubes has an outboard end 38 and an inboard end 40. The outboard end of the conduit tubes are sized to be receivably fit into, and held securely in place within, the internal diameter of the tapered end of the main prong assembly.

Next provided is a main oxygen delivery tube 42. It is fabricated of a flexible elastomeric material and has a round, hollow cylindrical shape. The delivery tube has an internal surface and an external surface with a wall thickness there between. It also has an outboard end 44 and an inboard end 46 with a length 48 there between. The main tube is sized to receive and retain the inboard ends of the pair of conduit tubes within the internal diameter of the outboard end of the main tube.

Next provided is an adhesive coupling means to secure the conduit tubes within the outboard end internal diameter of the main tube.

Next provided is an adjustment sleeve 50. The sleeve has a round hollow cylindrical configuration. It is fabricated of an elastomeric material and has an internal surface and an external surface with a wall thickness there between. The sleeve has an internal diameter sufficient to allow the adjustment sleeve to be slid with a minimal resistance along the external diameter of the main oxygen tube on to the pair of conduit tubes. The sleeve functions to tighten the cannula in place on the patient, when in use.

Next provided is a flared end piece 52. The end piece is fabricated of an elastomeric material. It has a tapered, hollow cylindrical shape. It has an internal surface and an external surface with a wall thickness there between. The flared end piece also has an inboard end 54 and an outboard end 56. The outboard end has an internal diameter sized to securely receive the external diameter of the inboard end of the main oxygen delivery tube. The inboard end is sized to have an internal diameter of between about 5 and 7 millimeters.

Next provided is a gas machine adapter 58. The adapter is fabricated of a rigid material. It has an oxygen line portion 60 and a gas machine portion 62. The oxygen line portion has a generally tapered hollow round cylindrical configuration. It has an inboard end 64 and an outboard end 66. The taper of the oxygen line portion of the gas machine adapter decreases from inboard to outboard. The adapter has an internal surface and an external surface and a wall thickness there between. The internal surface is smooth and the external surface of the oxygen line portion has a series of concentric steps 68 along the axis of the taper of the oxygen line portion. The inboard end of the oxygen line portion joins, and is coupled to, the gas machine portion.

The gas machine portion of the gas machine adapter has a generally round, hollow, cylindrical shape. It has an external surface and an internal surface with a wall thickness there between. The gas machine portion has an inboard end 70 and an outboard end 72. The internal diameter of the inboard gas machine portion of the adapter is between about 7 and 12 millimeters. The gas machine portion of the adapter has a knurled surface 74 on the outboard end of the gas machine portion. The knurled surface acts to facilitate the gripping of the gas machine portion.

Next provided is a gas machine 76 with a gas machine outlet 78 having a round hollow cylindrical configuration. The outlet has an internal surface and an external surface. The outlet has an internal diameter of between about 10 and 20 millimeters.

Next provided is a gas sampling conduit 80. The conduit is fabricated of a flexible elastomeric material and has a generally round, hollow, cylindrical configuration. The conduit has an outside diameter of between about 1 and 4 millimeters. The conduit has an internal surface and an external surface and a wall thickness of between. The thickness of the wall is between about 1 and 3 millimeters. The conduit has an inboard end 82 and an outboard end 84. The gas sampling conduit has an overall length of between about 4 and 6 feet. The outboard end has a pair of conduit nasal prongs 86. These prongs are oriented perpendicular to the long axis of the cylindrical hollow gas sampling conduit. In an alternative configuration each of the prongs 87 may run with each of the oxygen conduit tubes.

Next provided is an adherent means by which the gas sampling prongs are aligned with, and adherent to, the nasal prongs. The adherent means couples the gas sampling conduit in alignment with the oxygen conduit tube. The gas sampling conduit runs with, and is adherent to, the oxygen conduit tube to the point of juncture with the main oxygen delivery tube. The gas sampling conduit passes through, and is contained within, the adjustment sleeve. The gas sampling conduit then runs with, and is adherent to, the main oxygen tube to a point between about 10 and 15 inches from the inboard end. The adherent means keeps the gas sampling conduit coupled to the external surface of the nasal oxygen prongs, oxygen conduit and main oxygen tube.

Next provided is a gas sampling conduit end piece 88. The end piece has a generally hollow, round cylindrical configuration. It has an internal surface and an external surface and a wall thickness there between. The end piece has an inboard end 90 and an outboard end 92. The outboard end has an internal diameter sized to receive and securely hold the inboard end of the gas sampling conduit. The inboard end of the end piece has a female thread on the internal surface and is configured to receive a luer locking connector.

Lastly, there is provided a capnograph 94. The capnograph has a male luer lock connector 96 to receive, and mate with, the female luer locking connector of the conduit end piece.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An Oxygen delivery and gas sensing nasal cannula system for safely and conveniently providing oxygenation and gas analysis when in use, comprising, in combination;

a pair of nasal prongs fabricate of a flexible elastomeric material and having a hollow round cylindrical shape with an internal surface and an external surface with a wall thickness there between, with each nasal prong having an inboard end and outboard end with the outboard end being toward the user;

a main prong assembly fabricate of a flexible elastomeric material and having a hollow round cylindrically shaped body with two ends, and having an internal surface and an external surface and a wall thickness there between and having each of the ends configured with a taper, with each taper having an axial aperture, the main prong assembly also having two radial output apertures located on either side of and near the midpoint of the assembly with the apertures sized to firmly receive the inboard ends of the nasal prongs;

an adhesive coupling means to secure the inboard ends of the nasal prongs to the main prong assembly;

a pair of oxygen conduit tubes fabricated of a flexible elastomeric material having a continuously round, hollow cylindrical shape and having an internal surface with an internal diameter of between about 3 and 7 millimeters, and an external surface with an external diameter and a wall thickness there between, with each oxygen conduit tube having an outboard end and an inboard end, the conduit tubes being sized to have the external diameter of the outboard end receivably fit into and held securely in place within the internal diameter of the tapered end of the main prong assembly;

an adhesive means to couple the outboard ends of the oxygen conduit tubes to the tapered axial apertures of the main prong assembly;

a main oxygen delivery tube fabricate of a flexible elastomeric material having a continuous round, hollow cylindrical shape with an internal surface with an internal diameter, and an external surface with an external diameter with a wall thickness there between and having an outboard end and an inboard end with a length there between, the main tube being sized to receive and retain the inboard ends of the pair of oxygen conduit tubes within the internal diameter of the outboard end of the main tube;

an adhesive coupling means to secure the inboard ends of the conduit tubes within the internal diameter of the outboard end of the main tube;

an adjustment sleeve having a round hollow cylindrical configuration fabricated of an elastomeric material having an internal surface and an external surface with a wall thickness there between and having an internal diameter sufficient to allow the adjustment sleeve to be slid with a small resistance along the external diameter of the pair of conduit tubes thereby allowing the user to tighten and secure the cannula system in place when in use;

a flared end piece fabricated of an elastomeric material having a tapered, hollow cylindrical shape with an internal surface and an external surface with a wall thickness there between and having an inboard end and an outboard end, with the outboard end having an internal diameter sized to securely receive the external diameter of the inboard end of the main oxygen delivery tube and the inboard end being sized to have an internal diameter of between about 5 and 7 millimeters;

a gas machine adapter fabricated of a rigid material having an oxygen line portion and a gas machine portion, the oxygen line portion having an generally tapered hollow round cylindrical configuration having an inboard end and an outboard end with the taper decreasing from inboard to outboard, with an internal surface and an external surface and a wall thickness there between, the internal surface being smooth and the external surface having a series of concentric decreasing steps along the axis of the taper of the oxygen line portion, with the inboard end of the oxygen line portion joining the gas machine portion, the gas machine portion having a generally round, hollow, cylindrical shape with an external surface and an internal surface with a wall thickness there between, the gas machine portion also having an inboard end and an outboard end, the external diameter of the inboard end of the gas machine portion being between about 7 and 20 millimeters, with there being a knurled surface on the outboard end of the gas machine portion to facilitate the gripping of the gas machine portion;

a gas machine having a gas machine outlet with the outlet having a round hollow cylindrical configuration with an internal surface and an external surface, with the outlet having an internal diameter of between about 7 and 20 millimeters;

a gas sampling conduit having a generally round, hollow continuous cylindrical configuration having an external surface with an external diameter of between about 21 and 4 millimeters and an internal surface with an internal diameter of between about 0.5 and 3 millimeters, the gas sampling conduit having a wall thickness of between about 0.25 and 2 millimeters, with the gas sampling conduit having an inboard end and an outboard end, with the outboard end having a pair of nasal conduit sampling prongs with the sampling prongs having a cross sectional configuration similar to the gas sampling conduit and oriented perpendicular to the long axis of the cylindrical hollow gas sampling conduit and with the gas sampling conduit having an overall length of between about 4 and 6 feet;

an adherent means by which the gas sampling conduit is aligned with and adherent to the nasal prongs and the assembly body and the oxygen conduit tube and the main oxygen delivery tube, with the gas sampling conduit running with and being adherent to an oxygen conduit tube to the point of juncture with the main oxygen delivery tube, passing through and contained within the adjustment sleeve, with the gas sampling conduit then running with and being adherent to the main oxygen tube to a point between about 10 and 15 inches from the inboard end, the adherent means keeping the conduit attached to the external surface of the prongs and conduit and main oxygen tube;

a gas sampling conduit end piece having a generally hollow round cylindrical configuration with an internal surface and and external surface and a wall thickness there between and having an outboard end and an inboard end with the outboard end having an internal diameter sized to receive and securely hold the inboard end of the gas sampling conduit, with the outboard end having a female thread on the internal surface and configured to receive a luer locking connector;

a capnograph with a male luer lock connector to receive and mate with the luer locking connector of the inboard end of the conduit end piece to connect to and allow the passage of aspirated gases between the outboard end of the gas conduit tube and the capnograph.

2. An oxygen delivery and gas sensing nasal cannula system wherein the system further comprises:

a main prong assembly having a hollow round cylindrical shape;

a pair of nasal prongs coupled to the main prong assembly;

a pair of oxygen conduit tubes secured to the main prong assembly:

a main oxygen delivery tube being secured to the oxygen conduit tubes;

a gas sampling conduit having an inboard and an outboard end, the conduit being coupled with and running with the nasal prongs and running the length of the main oxygen delivery tube, the conduit having an end piece; and a flared main oxygen delivery tube end piece to be receivable coupled to an oxygen supply;

a gas machine adapter having an oxygen line portion and a gas machine portion, the oxygen line portion having a generally tapered hollow round cylindrical configuration with a series of concentric steps along the axis of the taper, and with a knurled surface to facilitate the gripping of the adapter;

a gas machine with a gas machine outlet having an internal diameter sized to securely receive the gas machine adaptor;

a gas sampling conduit end piece having an inboard end and an outboard end with a generally hollow, round cylindrical configuration with an internal surface and an external surface, and sized to receive and securely hold the inboard endo the gas sampling conduit on the outboard end of the end piece, with the inboard end of the end piece having a female thread on the internal surface and configured to receive a luer locking connector; and a capnograph with a male luer locking connector to receive and mate with the luer locking connector of the conduit end piece.

* * * * *